tion signals to cells of the retina, wherein the stimulation elements (17) are designed as radiation-emitting elements.

(12) United States Patent
Wrobel et al.

(10) Patent No.: US 9,162,060 B2
(45) Date of Patent: Oct. 20, 2015

(54) ACTIVE RETINAL IMPLANT

(75) Inventors: Walter G. Wrobel, Reutlingen (DE); Eberhart Zrenner, Tuebingen (DE); Albrecht Rothermel, Neu-Ulm (DE)

(73) Assignee: Retina Implant AG, Reutlingen (DE)

( * ) Notice: Subject to any disclaimer, the term of this patent is extended or adjusted under 35 U.S.C. 154(b) by 853 days.

(21) Appl. No.: 13/236,569

(22) Filed: Sep. 19, 2011

(65) Prior Publication Data

US 2012/0130302 A1 May 24, 2012

Related U.S. Application Data

(63) Continuation of application No. PCT/EP2010/001126, filed on Feb. 24, 2010.

(30) Foreign Application Priority Data

Mar. 20, 2009 (DE) .......................... 10 2009 015 389

(51) Int. Cl.
| | |
|---|---|
| *A61F 2/16* | (2006.01) |
| *A61N 1/00* | (2006.01) |
| *A61N 1/36* | (2006.01) |
| *A61N 1/05* | (2006.01) |

(52) U.S. Cl.
CPC .......... *A61N 1/36046* (2013.01); *A61N 1/0543* (2013.01)

(58) Field of Classification Search
USPC ....................................................... 623/6.63
See application file for complete search history.

(56) References Cited

U.S. PATENT DOCUMENTS

| | | | |
|---|---|---|---|
| 4,417,581 | A | 11/1983 | Dawson |
| 5,836,996 | A | 11/1998 | Doorish |
| 6,032,062 | A | 2/2000 | Nisch |
| 6,275,735 | B1 | 8/2001 | Jarding et al. |
| 6,315,940 | B1 | 11/2001 | Nisch |
| 6,427,087 | B1 | 7/2002 | Chow et al. |
| 6,458,157 | B1 | 10/2002 | Suaning |
| 7,003,354 | B2 | 2/2006 | Chow et al. |
| 7,321,795 | B2 * | 1/2008 | Bogdanowicz ................. 607/53 |
| 7,979,134 | B2 | 7/2011 | Chow et al. |
| 2002/0150933 | A1 | 10/2002 | Ehricht et al. |
| 2003/0068613 | A1 | 4/2003 | Leibrock et al. |
| 2004/0176820 | A1 | 9/2004 | Paul |
| 2005/0064469 | A1 | 3/2005 | Schulz et al. |

(Continued)

FOREIGN PATENT DOCUMENTS

| | | |
|---|---|---|
| DE | 195 29 371 | 2/1997 |
| DE | 197 12 309 | 3/1997 |

(Continued)

OTHER PUBLICATIONS

International Search Report and Written Opinion for International Application No. PCT/EP2012/066411 issued Dec. 3, 2012, 10 pages.

(Continued)

*Primary Examiner* — Thomas J Sweet
*Assistant Examiner* — Tiffany Shipmon
(74) *Attorney, Agent, or Firm* — Morrison & Foerster LLP

(57) ABSTRACT

An active retinal implant (10) to be implanted into an eye has an array (16) of stimulation elements (17) that emit stimulation signals to cells of the retina, wherein the stimulation elements (17) are designed as radiation-emitting elements.

23 Claims, 8 Drawing Sheets

(56) References Cited

U.S. PATENT DOCUMENTS

| | | |
|---|---|---|
| 2006/0078929 A1 | 4/2006 | Bickel et al. |
| 2006/0184214 A1 | 8/2006 | McDaniel |
| 2006/0184245 A1 | 8/2006 | Graf et al. |
| 2007/0053996 A1 | 3/2007 | Boyden et al. |
| 2007/0123766 A1 | 5/2007 | Whalen, III et al. |
| 2008/0288021 A1 | 11/2008 | Schmid |
| 2009/0011536 A1 | 1/2009 | Zhang et al. |
| 2009/0192571 A1 | 7/2009 | Stett et al. |
| 2009/0222062 A1 | 9/2009 | Rothermel |
| 2011/0238134 A1 | 9/2011 | Chow et al. |

FOREIGN PATENT DOCUMENTS

| | | |
|---|---|---|
| DE | 102 01 463 | 7/2003 |
| DE | 103 15 074 | 10/2004 |
| DE | 10 2006 048 819 | 4/2008 |
| EP | 0 460 320 | 8/1990 |
| EP | 2 289 594 | 3/2011 |
| WO | WO-01/02094 | 1/2001 |
| WO | WO-01/65251 | 9/2001 |
| WO | WO-2004/067088 | 8/2004 |
| WO | WO-2004/067734 | 8/2004 |
| WO | WO-2005/000395 | 1/2005 |
| WO | WO-2007/121901 | 11/2007 |
| WO | WO-2007/128404 | 11/2007 |
| WO | WO-2008/037362 | 4/2008 |
| WO | WO-2008/089003 | 7/2008 |
| WO | WO-2010/105728 | 9/2010 |
| WO | WO-2011/086150 | 7/2011 |

OTHER PUBLICATIONS

Examination Report for DE 10 2009 061 008.1, issued Oct. 22, 2013, 7 pages.
Restriction Requirement for U.S. Appl. No. 13/199,904, mailed Nov. 1, 2013, 9 pages.
Office Action for U.S. Appl. No. 13/199,904, mailed Dec. 31, 2013, 12 pages.
Final Office Action in U.S. Appl. No. 13/199,904, mailed Jul. 21, 2014, 13 pages.
Request for Continued Examination in U.S. Appl. No. 13/199,904, dated Sep. 18, 2014, 14 pages.
International Preliminary Report on Patentability for International Application No. PCT/EP2010/001126, issued Sep. 20, 2011, 12 pages.
International Search Report for International Application No. PCT/EP2010/01126, issued Sep. 20, 2010, 17 pages.
Chow et al., "The Artificial Silicon Retina Microchip for the Treatment of Vision Loss from Retinitis Pigmentosa," Archives of Opthalmology (2004) 122:460-469.
Dawson et al., "Improved Electrode for Electroretinography," Investigative Opthalmology & Visual Science (1979) 18(9) 988-991.
Fujikado et al., "Effect of Transcorneal Electrical Stimulation in Patients with Nonarteritic Ischemic Optic Neuropathy or Traumatic Optic Neuropathy," Japanese Journal of Opthalmology (2006).
Gall et al., "Noninvasive Transorbital Alternating Current Stimulation Improves Subjective Visual Functioning and Vision-Related Quality of Life in Optic Neuropathy," Brain Stimulation (2011) 4:175-188.
Gekeler et al., "Phosphenes Electrically Evoked with DTL Electrodes: A Study in Patients with Retinitis Pigmentosa, Glaucoma, and Homonymous Visual Field Loss and Normal Subjects," Investigative Opthalmology & Visual Science (2006) 47(11) 4966-4974.
Lagali et al., "Light-Activated Channels Targeted to ON Bipolar Cells Restore Visual Function in Retinal Degeneration," Nat. Neurosci. (2008) 11(6):667-675.
Schatz et al., "Transcorneal Electrical Stimulation for Patients with Retinitis Pigmentosa—a Prospective, Randomized, Sham-Controlled Exploratory Study," Investigative Opthalmology & Visual Science (published online Apr. 5, 2011) Manuscript iovs 10-6932.
Vogel et al., "Optoelektronische Bauelemente mit Integriertem Lichtemitter," Elektronik (2009) 54-58 (with English abstract).
Office Action for U.S. Pat. No. 6,427,087 B1, dated Sep. 20, 2001.
Original claims of U.S. Appl. No. 10/142,277, May 9, 2002.
Preliminary Amendment for U.S. Pat. No. 7,003,354 B2, dated Sep. 10, 2002.
Supplemental Preliminary Amendment for U.S. Pat. No. 7,003,354, dated Sep. 11, 2003.
Office Action for U.S. Pat. No. 7,003,354, dated Apr. 8, 2005.
Original claims for U.S. Appl. No. 11/293,871, Dec. 2, 2005.
Amendment for U.S. Pat. No. 7,979,134 B2, dated Sep. 9, 2008.
Final Office Action for U.S. Pat. No. 7,979,134 B2, dated Jan. 27, 2009.
Office Action for U.S. Pat. No. 7,979,134 B2, dated Jul. 30, 2009.
Amendment for U.S. Pat. No. 7,979,134 B2, dated Nov. 30, 2009.
Final Office Action for U.S. Pat. No. 7,979,134 B2, dated Feb. 18, 2010.
Amendment for U.S. Pat. No. 7,979,134 B2, dated May 18, 2010.
Office Action for U.S. Pat. No. 7,979,134 B2, dated Jun. 9, 2010.
Amendment for U.S. Pat. No. 7,979,134 B2, dated Oct. 11, 2010.
Amendment for U.S. Pat. No. 7,979,134 B2, dated Jun. 25, 2009.
Notice of Allowance for U.S. Pat. No. 7,979,134 B2, dated Mar. 10, 2011.
Office Action for US Publication No. 2011/238134 A1, dated Sep. 1, 2011.
Amendment for US Publication No. 2011/238134 A1, dated Nov. 30, 2011.
Final Office Action for US Publication No. 2011/238134 A1, dated Jan. 31, 2012.
Original claims for U.S. Appl. No. 09/564,841, May 4, 2000.
Response for European Patent Application No. EP 2 289 594 A1, dated Sep. 2, 2011.

* cited by examiner

ACTIVE RETINAL IMPLANT

This is a continuation application of copending international patent application PCT/EP 2010/001126, filed Feb. 24, 2010 and designating the United States, which was published in English as WO 2010/105728 A2, and claims priority to German patent application DE 10 2009 015 389.6, filed Mar. 20, 2009. The content of these prior applications are incorporated herein by reference in their entirety.

BACKGROUND OF THE INVENTION

1. Field of the Invention

The present invention relates to an active retinal implant to be implanted into an eye, with an array of stimulation elements that emit stimulation signals to cells of the retina.

2. Related Prior Art

By way of example, such a retinal implant has been disclosed in WO 2005/000395 A1.

The known retinal implant serves to counteract a loss of vision due to degenerations of the retina. Here, the basic idea is to implant into the eye of a patient a microelectronic stimulation chip that replaces the lost vision by electrical excitation of neurons.

In doing so, there are two different approaches as to how such retinal prostheses can be designed.

The subretinal approach described in WO 2005/000395 A1, mentioned at the outset, and in e.g. EP 0 460 320 A2 uses a stimulation chip, implanted into the subretinal space between the outer retina and the pigment epithelium of the retina, that converts ambient light, impinging on an array of photodiodes integrated in the stimulation chip, into electrical stimulation signals for neurons. These stimulation signals actuate an array of stimulation electrodes, which stimulate the neurons of the retina with spatially resolved electrical stimulation signals corresponding to the image information "seen" by the array of photodiodes.

Thus, this retinal implant stimulates the remaining, intact neurons of the degenerated retina, that is to say horizontal cells, bipolar cells, amacrine cells and possibly ganglion cells as well. The visual image incident on the array of photodiodes or more-complex elements is, in the process, on the stimulation chip converted into an electrical stimulation pattern. This stimulation pattern then leads to the electrical stimulation of neurons, by means of which the stimulation is then guided to the ganglion cells in the inner retina and, from there, led into the visual cortex via the optic nerve. In other words, the subretinal approach utilizes the natural interconnection of the previously present and now degenerated or lost photoreceptors with the ganglion cells in order to supply the visual cortex with nerve impulses, which correspond to the seen image, in a conventional fashion. Thus, the known implant is a replacement for the lost photoreceptors and it, like the latter, converts image information into electrical stimulation patterns.

In contrast thereto, the epiretinal approach utilizes a device, consisting of an extra-ocular and an intra-ocular part, which communicate with one another in a suitable fashion. The extra-ocular part comprises a camera and a microelectronic circuit for coding captured light, that is to say the image information, and transmitting it to the intra-ocular part as a stimulation pattern. The intra-ocular part comprises an array of stimulation electrodes, which contacts neurons of the inner retina and thus directly electrically stimulates the ganglion cells situated there.

A large number of publications disclose that the transmission of the electrical stimulation signals from the stimulation electrodes to the contacted cells, required in these implants, requires particular attention. This is because the coupling between a stimulation electrode and the contacted tissue is capacitive and so only transient signals can be used for electrical stimulation. This capacitive coupling is based on the fact that a capacitance (Helmholtz double layer) is formed in the eye at the boundary between the electrode and electrolyte as a result of the electrode polarization. Against this background, the stimulation signals are transmitted as pulses.

In the subretinal implant as per WO 2005/000395, mentioned at the outset, the incident light is therefore converted into voltage pulses with a pulse length of approximately 500 microseconds and a pulse spacing of preferably 50 milliseconds, such that a repetition frequency of 20 Hz results, which was found to be sufficient for flicker-free vision. In doing so, the pulse spacing moreover is sufficient to restore the electrode polarization completely.

WO 2007/128404 A1 deals with the question as to how the perception can be further improved by a suitable choice of pulse length and repetition frequency of the electrical stimulation signals. Starting from experimental findings using implanted subretinal implants, it proposes to subdivide the multiplicity of stimulation electrodes into at least two groups of stimulation electrodes, which are actuated over time, one after another, in order to emit stimulation signals.

Thus, the seen image is not imaged as a whole on the stimulation electrodes with a high repetition frequency; rather, the image is decomposed, so to speak, into at least two partial images, which are alternately "switched-through" at a lower repetition frequency to the stimulation electrodes.

By way of example, if four partial images, each with a repetition frequency of 5 Hz, are emitted as stimulation signals from, in each case, a quarter of the stimulation electrodes, a new (partial) image in the form of stimulation signals, that is to say pulses, is nevertheless emitted to the cells of the retina by the stimulation electrodes, respectively with a partial image frequency of 20 Hz.

This may slightly reduce the spatial resolution, but the image repetition frequency of 20 Hz required for physiologically flicker-free vision is achieved.

Depending on the number and local "density" of the stimulation electrodes, it is also possible to use a larger number of partial images in the process, provided that the desired spatial resolution is achieved as a result of this. In the case of a larger number of partial images, the repetition frequency of the individual partial images can then be further reduced, wherein, nevertheless, a new partial image in the form of a pattern of stimulation pulses is emitted every 50 milliseconds, i.e. with an image repetition frequency of 20 Hz.

A further problem in the known retinal implants is the energy supply of the stimulation chip.

That is to say, the energy for generating the electrical stimulation signals cannot be obtained from the incident useful light itself, even in subretinal implants, and so additional external energy is required. Here, this external energy is either obtained from additional invisible light irradiated into the eye, coupled in from the outside by means of e.g. a coil, or conducted by a wire led into the eye.

The implant known from WO 2005/000395 A1 is supplied with electrical energy, without the need for wires, by irradiated IR light or inductively coupled RF energy, wherein information for controlling the implant may be contained in this external energy supplied from the outside.

However, since wireless retinal implants for human applications that have a satisfactory quality are not currently available, at the moment use is made of not only epiretinal but also subretinal implants, which are supplied with the required external energy by wires.

WO 2007/121901 A1 describes e.g. a subretinal retinal implant, in which the external energy and control signals are guided by a wire to the stimulation chip implanted in the eye. Here, the wire is applied and fixed to the sclera of the eye in order to avoid forces on the implant.

Since, on the one hand, integrated circuits operated with DC voltage are generally available on the implants and, on the other hand, there is little space on the implants themselves, most known implants are directly supplied with DC voltage. That is to say that, in the case of AC voltage supply, the rectifiers required on the implant would need too much space and also could not be implemented in integrated circuits in a technically expedient fashion, in particular due to the required smoothing capacitors.

However, in the long run, the wired transmission of DC voltage leads to electrolytic decomposition processes in the tissue surrounding the wire and so this method of supplying implants with external energy is also unsatisfactory.

Therefore, WO 2008/037362 A2 proposes to supply the implant with at least one substantially rectangular electrical AC voltage that, averaged over time, is at least almost without a DC voltage component in relation to the tissue mass. In the process, the potential level can be selected such that, averaged over time, the supply voltage is at least almost without a DC voltage component. This, at least to a large extent, avoids the bothersome electrolytic decomposition processes.

Despite the above-described promising approaches for solving the substantial technological problems in the context of epiretinal and, in particular, subretinal retinal implants, the currently available retinal implants do not yet satisfy possibly all requirements for comprehensive and satisfactory patient care.

Furthermore, it still remains to be investigated whether the epiretinal and/or subretinal approach is suitable for all patients suffering from visual impairment as a result of losing their natural photoreceptors, as is the case in retinits pigmentosa or in age-dependent macular degeneration.

U.S. Pat. No. 5,836,996A discloses a different retinal implant approach using a first layer of photodiodes that convert incident ambient light into electrical signals. These electrical signals control light emitting elements that emit optical signals that are received by a second layer of photodiodes. These second photodiodes convert the optical signals into electrical stimulation signals that are used to stimulate cells of the retina.

By this, an optical attenuator is provided that ensures that the level of the electrical stimulation signals is not such that they damage the retina. It is also disclosed to use only one layer of photodiodes that directly emit electrical stimulation asignals to retinal cells.

A recently expanding alternative to implanting a retinal implant of the type described thus far consists of a genetic treatment of patients suffering from a loss of their natural photoreceptors. In this approach, using genetic-engineering methods, light sensitive cytoplasmic channels are introduced into the still-present neurons of blind or visually impaired people, such that the electrical activity of the neurons can be modulated by irradiation with light, which causes a perception of light.

This approach is based on reports from different scientific groups, who used different derivatives of rhodopsin, usually found in bacteria, to control, by irradiation with light, ion channels in the cytoplasmic membrane of neurons in respect of the opening probability thereof. The transmembrane ion channels modified in this fashion could be introduced into different cell types of the retina, such as ganglion cells and bipolar cells, in which the modulation of the electrical activity leads to light perception in the visual centres.

In doing so, also rhodopsin derivatives with different spectral sensitivity were used for generating channels, which, introduced into ON bipolar cells or OFF bipolar cells by transgenic techniques, permit a separate actuation of the brightness coding ON bipolar cells and the darkness coding OFF bipolar cells as a result of different spectral light stimulation.

However, the light intensity required in order to be able to use light to modulate the electrical activity of neurons equipped with these rhodopsin-controlled channels is several orders of magnitudes greater than the light intensity required for the activation of the natural photoreceptors, i.e. the rods and cones; see Lagali et al.: "Light-activated channels targeted to ON bipolar cells restore visual function in retinal degeneration", Nature Neuroscience, volume 11, number 6, June 2008, pages 667-675, with further references therein.

Lagali et al. report that when using neuromodulators, genetically coded in this fashion, in ON bipolar cells at a light intensity of at least $10^{15}$ photons $cm^{-2}$ $s^{-1}$, light perception was noted in the ON path of the retina even when photoreceptors were absent. It should be noted at this point that $2.5 \times 10^{15}$ photons $cm^{-2}$ $s^{-1}$ at 500 nm correspond to approximately 1 mW $cm^{-2}$.

Comparable values were determined for ganglion cells. By contrast, the minimum intensities for rods and cones are only $10^{6}$ photons $cm^{-2}$ $s^{-1}$ and $10^{10}$ photons $cm^{-2}s^{-1}$, respectively.

Even if it seems possible to increase the light sensitivity of rhodopsin-controlled channels by up to three orders of magnitude, the sensitivity of the rods and cones will not be achievable under any circumstances, not even approximately, because the other cells of the retina, which are made light sensitive by rhodopsin, lack the particular amplifying mechanisms of the rods and cones.

SUMMARY OF THE INVENTION

Against this background, the inventors of the present application have recognized that the normal daylight is insufficient for being able to stimulate the neurons, which were made to be light sensitive, with light patterns in a spatially resolved fashion such that a corresponding optical perception is brought about in the visual centre.

In view of the above, the object underlying the present invention is to provide a retinal implant which takes into account these observations and which avoids or reduces disadvantages from the prior art.

According to the invention, this object is achieved in that, in the case of the active retinal implant mentioned at the outset, the stimulation elements are designed as radiation-emitting elements that emit optical stimulation signals for directly optically stimulating cells of the retina.

This implant is provided for patients whose neurons of the retina were previously equipped with light-sensitive channels, for example by transfection with (viral) vectors for the expression of channelrhodopsin-2, as reported by Lagali et al., loc. cit.

In such patients, the novel implant is inserted epiretinally or subretinally in order to optically stimulate in situ, so to speak, the cells, which were made to be light sensitive, in the direct vicinity thereof in a spatially resolved fashion with image information in a basically "optical fashion".

Due to the relatively low absorption of light radiation in the neurons, which were made to be light sensitive, as compared to the normal visual process, proceeding from the publication of Lagali et al. would first of all lead to the provision of devices like night-vision equipment, on the outside of the eye, that amplify incident light patterns to form light patterns with a sufficient brightness and then image these onto the cell populations on the fundus of the eye in a natural fashion by means of imaging via the lens. The amplifying power of this external device could be designed to be almost arbitrarily high.

However, the inventors avoided precisely this path because the use of external "light amplifiers", according to a realization of the inventors, would have fundamental disadvantages that do not occur in the novel solution.

External light amplifiers primarily have the disadvantage that the light energy required for the external stimulation of the neurons, which were made to be light sensitive, is so high that it can lead to damage in the eye, be it directly by phototoxic reactions or indirectly by development of heat.

The inventors were able to show that the optical conditions on the eye, in particular the losses due to the restriction of the solid angle, lead to not even 0.02% of the radiation emitted by an external array of radiation-emitting elements, e.g. a field of LEDs, reaching the retina.

If an acceptable irradiance of at most 200 mW/cm$^2$ in the visible spectrum were assumed for the retina, and an irradiated surface of 3 mm×3 mm, corresponding to a radiation power of 18 mW, the LED array would have to emit a radiation power of 120 W. Although this appears to be possible from a technical point of view, this does entail the risk of unforeseeable damage to the eye, particularly to the last possibly still remaining photoreceptors. Furthermore, such a device would only have limited acceptance due to the size and energy use thereof.

By contrast, an implanted LED array actually uses the entire light power, radiated into the semi-space, of the individual LEDs for illuminating the retina. Thus, there are no "optical" losses.

However, there are losses during the in situ conversion of electricity into light that contribute to the thermal load on the retina and said losses differ depending on the utilized technology and wavelength of the emitted radiation. These losses can be between 90% and 95%, but can possibly also be only 50% in currently available highly efficient LEDs or OLEDs.

If a maximum acceptable thermal load on the retina were assumed to be 200 mW/cm$^2$, then an LED array with a radiation surface of 3 mm×3 mm would be allowed to shine with at most 1 to 2 mW. This value can be increased significantly if the thermal power dissipation is distributed in the eye by suitable heat conduction surfaces.

A 3 mm×3 mm radiation surface with an optical power of 1 mW corresponds to approximately $27 \times 10^{15}$ photons cm$^{-2}$ s$^{-1}$ at 500 nm. This is approximately 27 times greater than the light intensity of at least $10^{15}$ photons cm$^{-2}$ s$^{-1}$ reported by Lagali et al. at which, in the absence of photoreceptors, a light perception is recorded in the ON path of the retina by modified neurons. This offers a large safety margin.

Therefore, the required light intensity can be provided by the novel implant without problems and without the risk of (further) damage to the retina or the remaining photoreceptors.

Therefore, the novel implant offers significant advantages over an external light amplifier but affords equal, if not better, stimulation.

Moreover, a subretinal implant affords small irradiation surfaces in close contact with the retina and so nonlinear behaviour, e.g. a stimulation threshold, of the neurons, which were made (also "modified" in the following text) to be light sensitive, to be taken into account. In this case, it is also possible to utilize partial images, which are offset in time and superimposed, as is known for the purely electrical stimulation disclosed in WO 2007/128404 A1, which was discussed at the outset and the disclosure whereof is herewith made the subject matter of the present invention by reference.

These partial images can each have a higher light intensity per unit area and so the individual modified neurons are stimulated by a sufficient light intensity, without the maximum acceptable thermal load on the retina being exceeded. This would not be possible using an external light amplifier.

A further advantage of the novel implant consists of the last possibly still intact photoreceptors not being damaged during practical use in humans. By contrast, because of the high irradiated light power when using external light amplifiers, there is the risk of these last photoreceptors being damaged; this is unacceptable from medical and, in particular, ethical points of view.

Moreover, there are further advantages because the novel implant directly abuts the retina, as will be explained below.

The object underlying the invention is completely achieved in this fashion.

An embodiment preferably provides for an image receiver that converts incident ambient light into spatially resolved electrical signals, which control the array of radiation-emitting elements.

These spatially resolved electrical signals therefore contain the image information required to actuate the array such that it reemits the image "seen" by the image receiver as an optical image and thus optically stimulates the modified neurons.

Here, the image receiver can be designed as an external image receiver, which is arranged outside of the eye.

Here, the externally recorded and further processed image information is transmitted to the implant in the form of electrical signals via wires or wirelessly, as is the case in the known epiretinal implants. At the implant, these signals are possibly processed further and reemitted by the array of radiation-emitting elements as an "internal image", which illuminates the modified neurons.

Here, the design details of the external image receivers, the processing electronics and the "data transmission" into the eye can be taken—possibly with an appropriate adaptation—from the known epiretinal implants.

Alternatively, the image receiver can also be designed as an implantable image amplifier, which is likewise implanted into the eye.

Thus, in this case, an image receiver and an array of "image transmitters" are implanted into the eye. This design, which seems unconventional at first sight, can surprisingly provide the required radiation energy for exciting the modified neurons without the risk of damaging the eye by irradiated light, as would be the case with an external light amplifier.

However, this alternative is connected to a further, significant advantage.

That is to say, in the case of a light amplifier or image receiver applied to the outside of the eye, the movement of the eyes, which satisfies an important function when finding objects, cannot be utilized. Thus, despite differing positions of the eyes, the patient would always see the same image as long as the patient's head does not move. This is confusing for the patient and, according to the findings of the inventors, this would reduce the use of the implant. Although the use of a so-called eye tracking control, which is intended to detect and utilize the eye movement, has already been suggested in the case of image receivers attached to the outside, this approach was found to be very complex, and there is no experience available yet as to whether this will be possible with sufficient accuracy.

However, if the image receiver is also implanted into the eye, the patient can use the natural eye movement and the head movement in the conventional fashion for viewing images and scanning for objects.

In doing so, the design details of the implanted arrays of photodiodes, the control and processing electronics and the energy transmission into the eye—possibly with an appropriate adaptation—can be taken from the subretinal implants mentioned at the outset, which is why the disclosure of the mentioned IP rights are herewith made to be the subject matter of the present application by reference.

In this case, it is preferable if the image receiver and the array of radiation-emitting elements are separate components.

In this case, it is advantageous that the components can be placed into the eye such that the scattered light emanating from the array of radiation-emitting elements is not directly incident on the image receiver and cannot be converted into electricity at said location, which would lead to positive feedback. Incidentally, this problem does not exist in the case of an external light amplifier or image receiver.

Thus, the scattered light problem in the implanted image receiver can for example be solved by the image receiver and image transmitter being spatially separated components that are implanted separately. This affords a geometric arrangement in the eye that allows for the scattered light problem.

In doing so, it is preferable if both components are arranged by/on a preferably flexible support.

The image receiver can then be arranged epiretinally, for example. The support is then led subretinally at the edge of the retina and so the image transmitter can be arranged under or else next to the image receiver.

On the other hand, it is preferable if the image receiver and the array of radiation-emitting elements are arranged next to one another by/on the support.

In this case, it is advantageous that, as a result of the geometric proximity, no scattered light from the image transmitter can reach the image receiver directly and this reduces the scattered light problem.

The support, preferably a film, is placed subretinally such that image transmitter and image receiver are situated next to one another in the subretinal space. This leads to a separation of image transmitter and image receiver of approximately 10°; the patient would perceive this like prismatic aberration, which can be corrected by prismatic spectacles or a simple strabismus operation.

On the other hand, it is preferable if the image receiver and the array of radiation-emitting elements are arranged one above the other.

In this case, it is possible for a smaller chip to be arranged on a larger chip, for example by flip-chip-bonding. Here, the problem of prismatic aberration does not occur or is less pronounced than in the other alternatives discussed thus far because the two components are arranged one above the other.

This implant can be inserted subretinally or epiretinally.

In the case of an epiretinal implant, the image receivers/photodiodes and the electronics are arranged on the top side of a silicon chip and a further chip, e.g. made of GaAlAs, which contains the image transmitters, can be arranged on the lower side. The two chips are interconnected by means of through contact.

A further advantage in this case is that the radiated light is partially absorbed by the natural pigment layer after it has passed through the retina and can only contribute a little to the scattered light.

In these alternatives, it is in each case advantageous overall that image transmitter and image receiver can be designed as separate chips using the respectively optimum technology for generating light (GaAs, InP, GaP) or for converting light into electricity and the electronic further processing thereof (Si).

On the other hand, it is preferable if the image receiver and the array of radiation-emitting elements are arranged integrated in a chip.

By way of example, this integration can be afforded by so-called OLEDs, which permit the integration of a highly efficient and stable light source into silicon; see Vogel and Amelung: "OLED on CMOS" in Electronik 1/2009, pages 54 to 58.

In this case, it is advantageous that the novel chip can be implanted more easily than an implant made of two chips or components, with the problem of prismatic aberration no longer occurring in this case either because the associated pixels of image transmitter and image receiver can be situated directly next to one another/above one another.

In this embodiment, the novel implant combines two opposing functions per se in a particularly advantageous fashion. It records an image like a camera chip and at the same time reradiates a corresponding image at the same location with a high intensity and accurate to within a pixel.

In general, it is preferable if the radiation-emitting elements emit electromagnetic radiation within and/or outside of the visible spectrum, particularly when the image receiver and the array of radiation-emitting elements operate in different regions of the electromagnetic spectrum.

This affords spectral separation of the "seen" and the "emitted" image, which further reduces the scattered light problem already discussed above.

In doing so, it is particularly preferable if the image receiver processes electromagnetic radiation in the visible region of the spectrum and the array of radiation-emitting elements radiates electromagnetic radiation outside of the visible region of the spectrum, preferably in the near infrared region.

Here, it is advantageous for the image receiver to record and process normal ambient light whereas the image emitted by the image transmitter is invisible and so the eyes of the patient do not "shine" in a fashion that can be perceived from the outside.

In this case, the radiation-emitting elements are preferably light-emitting diodes, e.g. infrared-emitting LEDs on the basis of GaAlAs, or those on an organic basis (OLEDs).

In general, it is still preferable if the image receiver is provided with an optical filter, which blocks the spectrum of electromagnetic radiation emitted by the array of radiation-emitting elements.

This measure also reduces the scattered light problem because the spectral separation of the viewed and emitted image is increased.

Furthermore, it is preferable if the elements in the array of radiation-emitting elements have a spacing between one another, in which different populations of neurons react separately.

Here, the array has dimensions of e.g. 3 mm×3 mm and supports a matrix-shaped arrangement of e.g. 40×40 or 100× 100 LEDs.

According to another embodiment, the image receiver and the array of radiation-emitting elements operate with a time offset.

This measure also reduces the scattered light problem in that the image recording is decoupled in terms of time from the image emission. This decoupling can be effected in terms of pixels, rows or images. An optical image is first of all recorded and processed, then, the image receiver is switched to "blind" and the processed image is emitted by the image transmitter.

Furthermore, it is preferable if the array of radiation-emitting elements comprises elements with different spectral radiation.

In this case, it is advantageous that directly neighbouring cell populations, which were modified by rhodopsin with different spectral sensitivities, can be actuated separately and this increases the resolution and/or the contrast of the seen image.

Furthermore, it is preferable if the elements in the array of radiation-emitting elements are provided in a defined geometric arrangement.

This arrangement can be in the shape of a matrix with rows and columns, or in the shape of a beam, in order to be able to generate different patterns that ensure optimum recognition.

In general, it is preferable if the elements are arranged at a distance of e.g. 50 nm from one another.

As mentioned above, the novel retinal implant is provided for patients in whom neurons of the retina were equipped with light-sensitive channels, for example by transfection with (viral) vectors for the expression of channelrhodopsin-2, as reported by Lagali et al., loc. cit. Of course, the novel retinal implant and the modified neurons have to be matched to one another in the process, particularly in respect of the spectral sensitivity.

According to the invention, in order to be able to test and improve the properties of the modified neurons, provision is made for a testing device for cells, cell cultures and/or organotypic cell aggregates, which were equipped with light-sensitive channels, e.g. by transfection with possibly viral vectors for the expression of e.g. channelrhodopsin-2, with an array of microelectrodes, on which the cells, cell cultures and/or organotypic cell aggregates are cultivated, an array of radiation-emitting elements, which illuminate the cells, cell cultures and/or organotypic cell aggregates in a spatially resolved fashion using electromagnetic radiation within and/or outside of the visible spectrum, an actuation device for actuating the array of radiation-emitting elements in order to emit spatially resolved electromagnetic radiation, and an evaluation unit for detecting and evaluating signals, which are emitted by the cells, cell cultures and/or organotypic cell aggregates to the microelectrodes upon illumination by the array of radiation-emitting elements.

Such arrays of microelectrodes are known per se; they are referred to as MEAs and are available commercially, e.g. from Multichannel Systems MCS GmbH, Aspenhaustraße 21, 72770 Reutlingen, Germany.

By way of example, MEAs are described in DE 195 29 371 A1, DE 197 12 309 A1, EP 1 309 856 A1 and DE 195 49 731 from the Naturwissenschaftliches und Medizinisches Institut Reutlingen, their respective disclosure herewith being made the subject matter of the present application.

The use of such MEAs for determining the QT interval in cultures of beating cardiac cells is described in, e.g. WO 2004/067734, the disclosure thereof herewith being made the subject matter of the present application.

Cells can be cultivated and manipulated on these MEAs, wherein the electrical signals emitted by the cells can be detected and evaluated by the evaluation unit. As per the present invention, cells, cell cultures and/or organotypic cell aggregates, which were equipped with light-sensitive channels, are cultivated on such an MEA and are, in the process, illuminated by spatially resolved electromagnetic radiation via an array of radiation-emitting elements.

This array can be actuated electrically by means of the actuation device, wherein the array of radiation-emitting elements from the novel retinal implant can also be used. Here, the image receiver from the novel retinal implant can also be utilized as actuation device.

The function and/or the efficiency of the light-sensitive channels and/or of the array of radiation-emitting elements can be determined and monitored on the basis of the measured signals, possibly in cooperation with the image receiver.

The novel testing device thus affords the testing ex vivo and, without trials on animals, the optimization of the modification of cells and/or the novel retinal implant or the essential components thereof.

Here, the array of radiation-emitting elements can be arranged above the cells, cell cultures and/or organotypic cell aggregates, or it can be integrated in the array of microelectrodes.

In view of the above, the present invention also relates to a testing device for a retinal implant, with an array of microelectrodes, on which cells, cell cultures and/or organotypic cell aggregates are cultivated, which were equipped with light-sensitive channels, e.g. by transfection with possibly viral vectors for the expression of e.g. channelrhodopsin-2, a retinal implant according to one of claims 1 to 18, which illuminates the cells, cell cultures and/or organotypic cell aggregates in a spatially resolved fashion with electromagnetic radiation within and/or outside of the visible spectrum, and an evaluation unit for detecting and evaluating signals, which are emitted by the cells, cell cultures and/or organotypic cell aggregates to the microelectrodes when the retinal implant is illuminated.

In view of the above, a further object of the invention concerns a method of treating a patient in need of such treatment, comprising the steps of introducing light sensitive channels into neurons of at least one eye of blind or visually impaired people, such that the electrical activity of the neurons can be modulated by irradiation with light, and implanting into the such treated eye the novel retinal implant.

In this method, it is preferred if rhodopsin or rhodopsin derivatives with different spectral sensitivity are used for generating light activated channels in ON bipolar cells and OFF bipolar cells by transgenic techniques, whereby preferably neurons of the retina are equipped with light-sensitive channels, for example by transfection with (viral) vectors for the expression of channelrhodopsin-2.

For achieving such modifications of the neurons, techniques can be used as e.g. disclosed by Lagali et al., loc. cit.

Further advantages emerge from the description and the attached drawing.

It is understood that the abovementioned features and those yet to be explained in the following text can be used not only in the respectively specified combination, but also in other combinations or individually, without departing from the scope of the present invention.

BRIEF DESCRIPTION OF THE DRAWINGS

An embodiment of the invention is illustrated in the drawing and will be explained in more detail in the following description. In the drawing.

DESCRIPTION OF PREFERRED EMBODIMENTS

Figure 1:
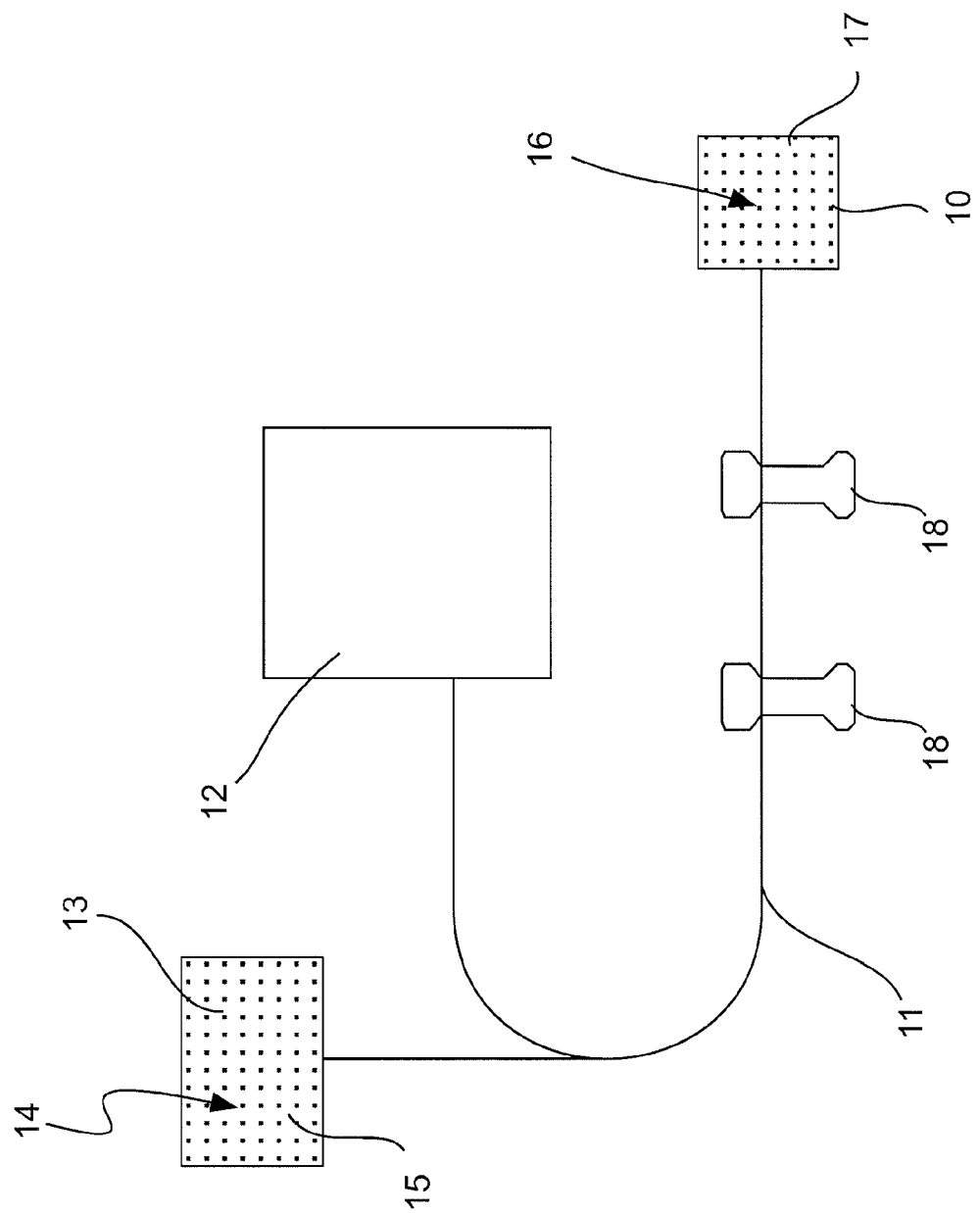
FIG. 1 shows a schematic illustration of a first embodiment of the novel retinal implant in an illustration that is not to scale.

FIG. 1 schematically illustrates a first embodiment of an active retinal implant 10, in which the dimensions have not been reproduced to scale.

A wire 11 is used to connect the retinal implant 10 to a supply unit 12 and an image receiver 13, with an array 14 of image cells 15 being arranged thereon and being designed, for example, as photodiodes. An array 16 of radiation-emitting stimulation elements 17 is arranged on the retinal implant 10 in order to output optical stimulation signals. By way of example, the stimulation elements 17 are designed as light-emitting diodes (LEDs).

The supply unit 12 supplies the retinal implant 10 with electrical energy and possibly with control signals, which can be used to influence or set different functions of the retinal implant.

The image receiver 13 uses the image cells 14 thereof for converting incident ambient light into spatially resolved electrical signals that are guided to the retinal implant 10 and are, at said location, converted back into optical signals, used to directly optically stimulate the modified cells in the retina, using the radiation-emitting stimulation elements 17.

Thus, the retinal implant 10 is provided for patients whose neurones of the retina were previously equipped with light-sensitive channels, for example by transfection with (viral) vectors for the expression of channelrhodopsin-2 as reported by Lagali et al., loc. cit.

In such patients, the retinal implant 10 is inserted epiretinally or subretinally in order to stimulate in situ, so to speak, the cells, which were made to be light sensitive, in the direct vicinity thereof in a spatially resolved fashion with image information in a basically "optical fashion".

Attachment clips 18 are provided on the wire 11, by means of which clips the wire 11 can be attached to the sclera of the eye of the person into whom the retinal implant 10 is implanted. This avoids forces from acting on the retinal implant 10, which forces could lead to a mechanical load on and/or a displacement of the retinal implant 10.

In the retinal implant 10 from FIG. 1, the image receiver 13 is arranged outside of the eye, for example in a pair of spectacles carried by the patient. The retinal implant 10 is then implanted epiretinally, for example, with it also being possible for energy, control signals and image information to be transmitted wirelessly, as is known, as such, from various publications.

Figure 2:
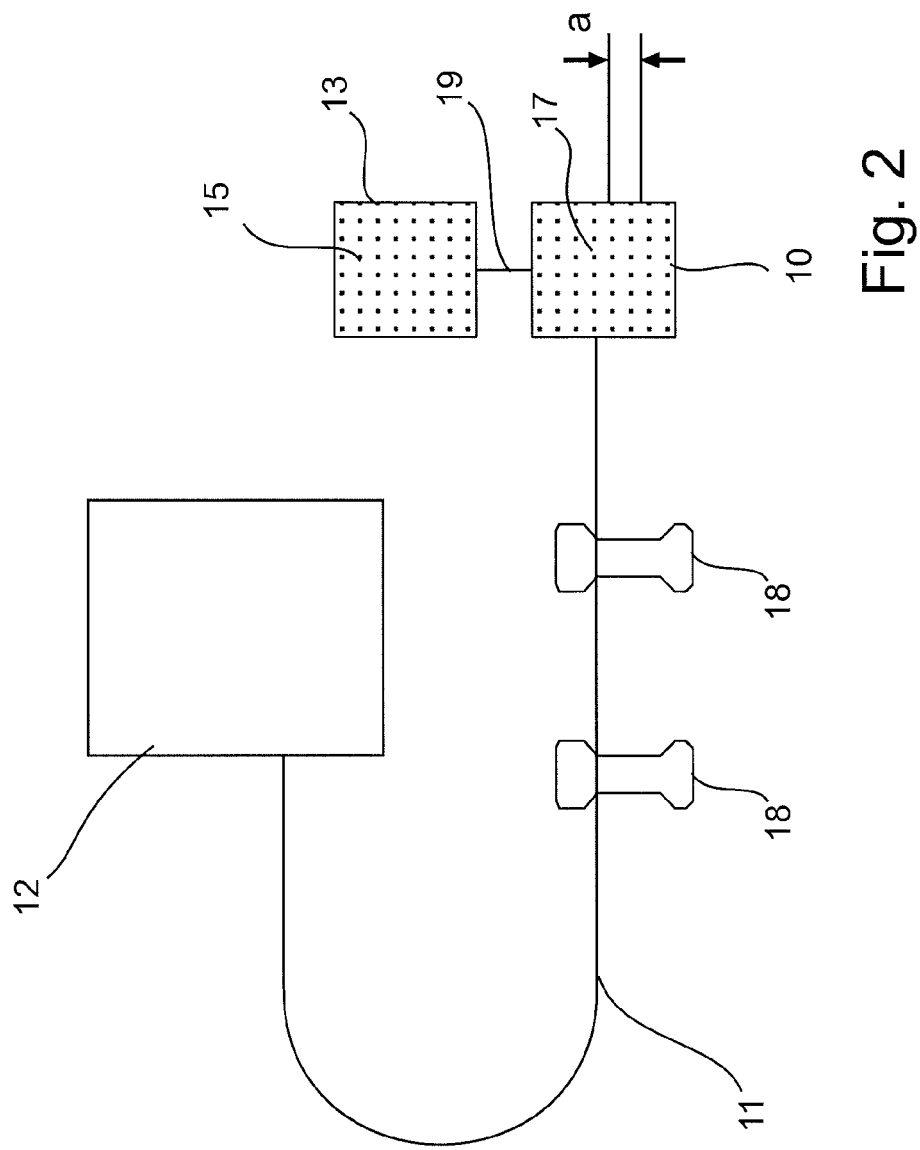
FIG. 2 shows a schematic illustration of a second embodiment of the novel retinal implant in an illustration that is not to scale.

However, in preferred embodiments, the image receiver 13 has an implantable design and so it is implanted into the eye, like the retinal implant 10 itself. This arrangement is shown in FIG. 2, where the image receiver 13 is arranged next to the retinal implant 10 to which it is connected by means of a wire 19.

As a result of this arrangement, the required radiation energy can be provided for exciting the modified neurones, without the risk of damage to the eye by irradiated light, as would be the case with an external light amplifier. This is because normal ambient light is sufficient for the image receiver 13 to convert the former into spatially resolved image signals by means of its image cells. These image signals are then reconverted into an optical image signal by the radiation-emitting (stimulation) elements 17, wherein the required electrical energy is provided by the control unit by means of the wire 11 or else wirelessly, for example via induction.

Since the image receiver is also implanted into the eye in this case, the patient can moreover use the natural eye movement and the head movement in the conventional fashion for viewing images and scanning for objects.

The design details of the implanted arrays of photodiodes, the control and processing electronics and the energy transmission into the eye—possibly with an appropriate adaptation—can be taken from the subretinal implants mentioned at the outset.

Figure 3:
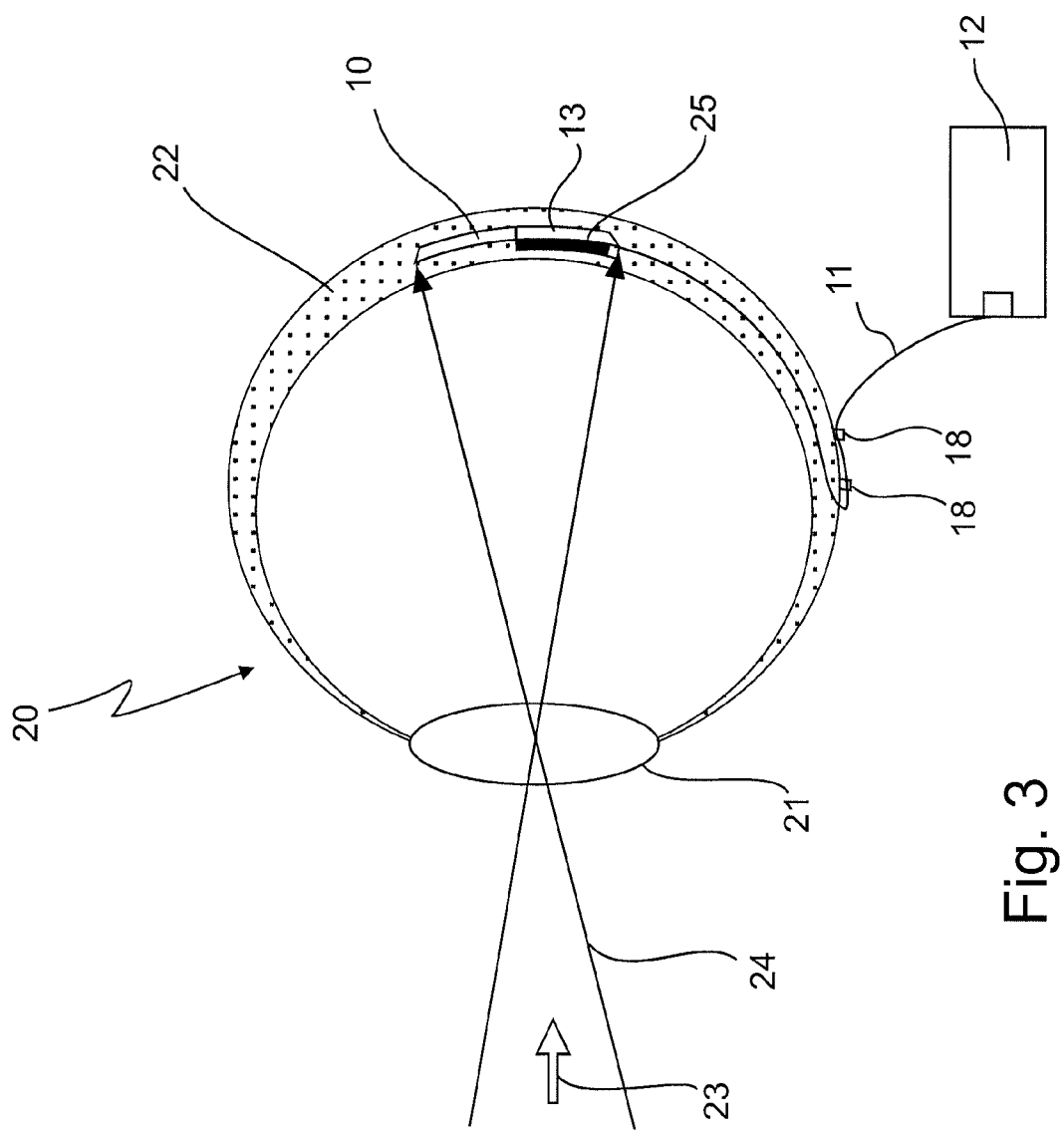
FIG. 3 shows a schematic illustration of a human eye into which the retinal implant as per FIG. 2 has been inserted; this illustration is likewise not to scale.

The retinal implant 10 and the image receiver 13 from FIG. 2 are designed to be implanted into a human eye 20, which is illustrated highly schematically in FIG. 3. For reasons of simplicity, only the lens 21 and the retina 22, into which the implant 10 and the image receiver 13 were implanted, are shown.

In the process, retinal implant 10 and image receiver 13 are preferably inserted into the so-called subretinal space that is formed between the pigment epithelium and the photoreceptor layer. If the photoreceptor layer is degenerated or lost, the subretinal space is formed between the pigment epithelium and the layer of bipolar and horizontal cells. Here, the retinal implant 10 is placed such that the stimulation elements 17 shown in FIG. 2 can radiate optical stimulation signals onto cells in the retina 22.

Visible light, which is indicated by an arrow 23 and the beam path of which is visible at 24, is guided via the lens 21 to the image receiver 13 where the visible light 23 is converted into electrical signals that are guided to the retinal implant 10 and converted into optical stimulation signals at said location.

As shown in FIG. 2, retinal implant 10 and image receiver 13 can be arranged next to one another in the process, wherein they can be designed as separate units using, for example, different technology. Both implants 10, 13 can in this case be arranged next to or above one another on a common film.

In order to avoid feedback by scattered light, the image receiver 13 can be arranged geometrically such that the light radiated by the retinal implant 10 can not feedback onto the image receiver, for what purpose provision can be made for the image receiver 13 to operate with light in the visible region of the spectrum, while the radiation-emitting elements 17 emit radiation outside of the visible spectrum, preferably in the near infrared region.

Alternatively or additionally, the image receiver 13 can be provided with an optical filter 25, which is indicated in FIG. 3 and blocks the optical radiation emitted by the retinal implant 10. This also reduces the scattered light problem because the spectral separation of a seen and an emitted image is increased.

In the process, the image receiver 13 and the array 16 of radiation-emitting elements 17 can be actuated such that the implants 10, 13 operate with a time offset.

This measure also reduces the scattered light problem in that the image recording is decoupled in terms of time from the image emission. This decoupling can be effected in terms of pixels, rows or images. An optical image is first of all recorded and processed, then, the image receiver is switched to "blind" and the processed image is emitted by the image transmitter.

The array 17 of radiation-emitting elements 16 can in this case comprise elements with different spectral radiation, and so directly neighbouring cell populations, which were modified by rhodopsin with different spectral sensitivities, can be actuated separately, and this increases the resolution and/or the contrast of the seen image.

Here, the elements 17 are provided in a defined geometric arrangement and have a spacing of 50 nm from one another; this distance is referred to by a in FIG. 2.

This arrangement can be in the shape of a matrix with rows and columns—as arranged in FIGS. 1 and 2—or in the shape of a beam in order to be able to generate different patterns that ensure optimum recognition.

FIG. 3 also shows that the wire 11 is guided out of the eye laterally and attached there, on the outside, to the sclera using the attachment clips 18 before the wire leads on to the external supply unit 12.

The supply unit 12 is then attached outside of the eye, e.g. on the skull of the patient (not shown in any more detail). The supply unit 12 sends electrical energy to the implant 10 and the image receiver 13, with control signals also being able to be transmitted simultaneously, which influence the operation of the implant as is described in, for example, WO 2005/00395 A1, mentioned at the outset, the contents of which are herewith made to be the subject matter of the present application.

The energy can in this case be supplied via substantially rectangular electrical AC voltages that, averaged over time, are almost without a DC voltage component relative to the tissue mass, as is described in WO 2008/037362, mentioned at the outset, the contents of which are herewith likewise made to be the subject matter of the present application.

Reference still has to be made to the fact that the dimensions of in particular the retinal implant 10, the image receiver 13, the attachment clips 18 and the external supply unit 12 are illustrated neither to scale nor in the correct dimensional relations to one another in FIGS. 1, 2 and 3.

Figure 4:
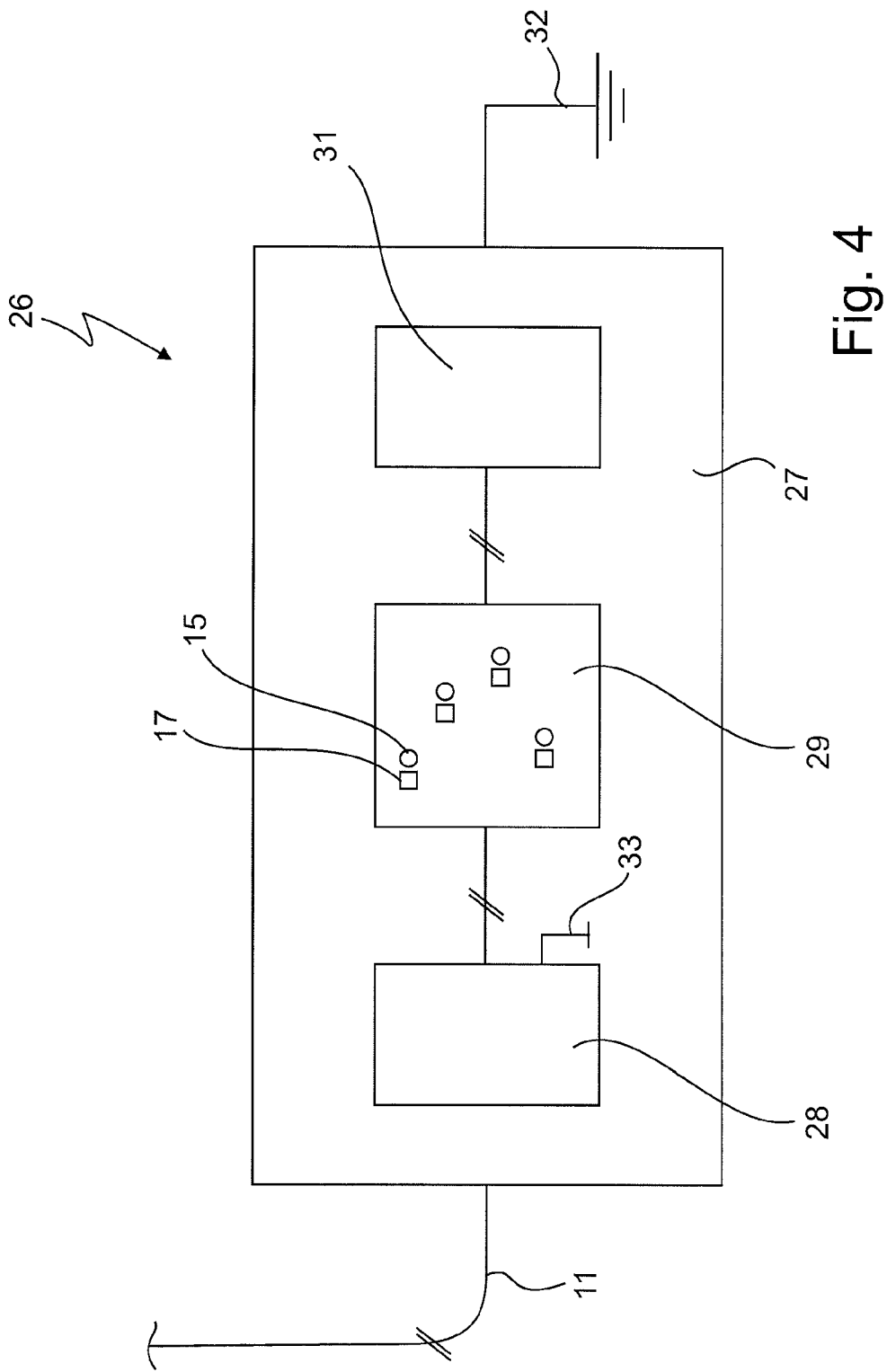
FIG. 4 shows a schematic illustration of a third embodiment of the novel retinal implant in an illustration that is not to scale.

Alternatively, image receiver 13 and retinal implant 10 can also be designed to be integrated in a chip 26, as is shown schematically in FIG. 4. By way of example, this integration is afforded by so-called OLEDs, which permit the integration of a highly efficient and stable light source into silicon, see Vogel and Amelung, loc. cit.

The chip 26 can be implanted more easily than an implant made of two chips or components, with prismatic aberrations not occurring in this case either because the associated pixels of image transmitter and image receiver can be situated directly next to one another/above one another.

In this embodiment, the novel implant combines two opposing functions per se in a particularly advantageous fashion. It records an image like a camera chip and at the same time reradiates a corresponding image at the same location with a high intensity and accurate to within a pixel.

The chip 26 has a film 27, on which an input stage 28 can be seen first of all, which is supplied with external energy from the outside via the wire 11. The input stage 28 is connected to a unit 29 that in this case has a multiplicity of image cells 17, which convert incident visible light into electrical signals that are then emitted as optical excitation patterns to neurons of the retina via the radiation-emitting stimulation elements 15 indicated next to the respective image cells 17.

The useful signals generated by the image cells 17 are processed in an output stage 31 that generates the corresponding optical stimulation signals, which are then led back to the stimulation elements 15.

In this context, reference is made to the fact that FIG. 4 is merely a schematic illustration of the chip 26, reproducing the logical design thereof; the actual geometric arrangement of the individual components can for example lead to each image cell 17 having an output stage in the direct neighbourhood thereof.

The chip 26 is connected to the tissue, into which the implant is inserted, via an external ground, indicated at 32. Furthermore, an internal electrical ground 33 is also indicated which is not connected to the external ground 32 in the illustrated embodiment.

Figure 5:
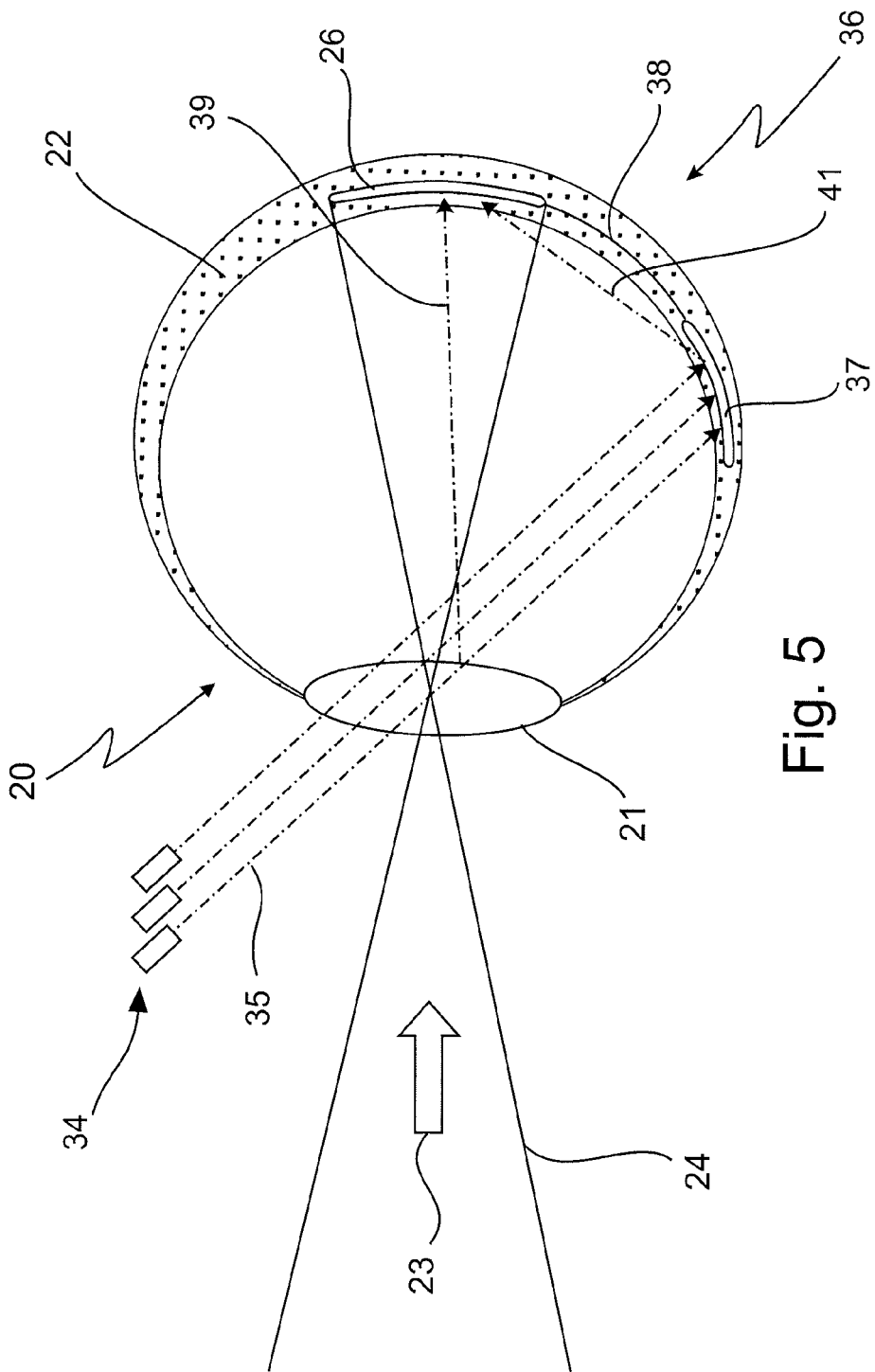
FIG. 5 shows a schematic illustration of a human eye into which the retinal implant as per FIG. 4 has been inserted; this illustration is likewise not to scale.

As an alternative to the wire-bound energy supply described thus far, the chip 26 can also be supplied with energy by means of infrared radiation, as is shown schematically in FIG. 5.

The chip 26 is implanted into the eye 20 of a patient, the lens 21 and the retina 22 of which are shown schematically as in FIG. 3. Visible light 23 passes through the lens 21 and into the eye according to the sufficiently well known laws of optics, wherein the beam path of the visible light 23 is again shown schematically by the reference sign 24.

Reference sign 34 is used to denote three IR laser diodes in an exemplary fashion; these can be used to couple energy in the form of IR radiation into the eye 20 in a targeted fashion. The infrared radiation is denoted by reference sign 35. The illustration with the aid of three IR laser diodes 34 is selected in an exemplary fashion in this case in order to show different beam paths.

In the embodiment shown in this case, the overall implant contains the actual stimulation chip 26, which is used to stimulate retinal cells in an optical fashion as a function of the visible light 23, and a radiation receiver 37 offset therefrom. Stimulation chip 26 and radiation receiver 37 are interconnected electrically which is illustrated here by a line 38. The radiation receiver 37 operates as an energy transducer (photovoltaic element) and absorbs the IR radiation 35, irradiated with the aid of the IR laser diodes 34, and provides energy for the stimulation chip 26 as a function thereof.

The spatial separation of stimulation chip 26 and radiation receiver 37, and the targeted irradiation of the IR radiation onto the radiation receiver already achieve a significant decoupling between stimulation chip 26 and radiation receiver 37. Such decoupling is desirable for preventing overdriving of the image cells 15 present in the stimulation chip 26 as a result of the IR radiation.

Furthermore, when the IR radiation 35 is irradiated into the eye 20, there are scattered components that can reach the stimulation chip 26 despite the spatial separation. A scattered beam 39, which is created as a result of refraction when the IR radiation 35 exits the lens 21, is shown in an exemplary fashion for two significant scatter sources. A further scattered beam 41 shows reflections on the surface of the radiation receiver 37. Moreover, multiple reflections can occur within the vitreous body of the eye 20 and so the stimulation chip 26 is subjected to IR scattered radiation from different directions and due to various causes. Thus, the stimulation chip 26 is provided with decoupling means that permit the separation of the invisible scattered radiation (IR radiation) 35 from incident visible light 23, as is described in great detail in WO 2004/067088 A1, the contents of which are herewith likewise made to be the subject matter of the present application.

Figure 6:
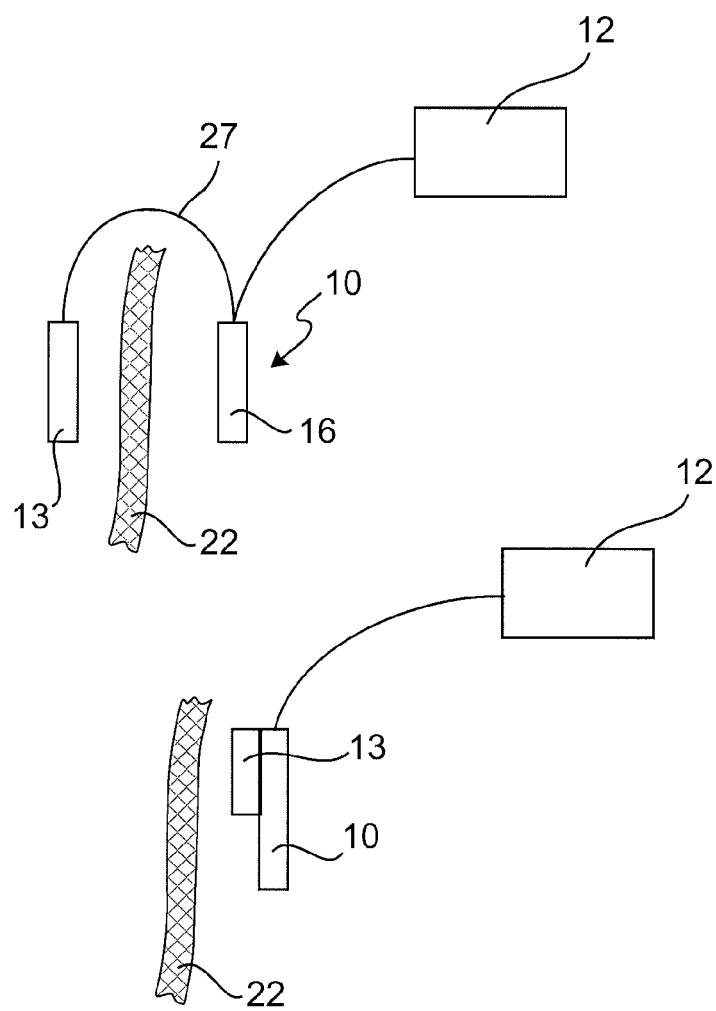
FIG. 6 shows two further embodiments for the arrangement of image receiver and array of stimulation elements.

FIG. 6 additionally shows two further embodiments for the arrangement of image receiver 13 and retinal implant 10 with the array 16 of stimulation elements.

At the top of FIG. 6, the two implants 10, 13 are interconnected by means of the flexible film 27, wherein the image receiver is arranged epiretinally and the array 16 is arranged subretinally.

At the bottom of FIG. 6, the image receiver 13 is arranged on the larger implant 10, with it conversely also being possible for the implant 10 to be arranged on the image receiver 13, which has the larger design.

In both cases, the implants 10, 13 are supplied with energy and control signals by means of the supply unit 12, wherein provision can also be made for a separate radiation receiver 37—as in FIG. 5.

Figure 7:
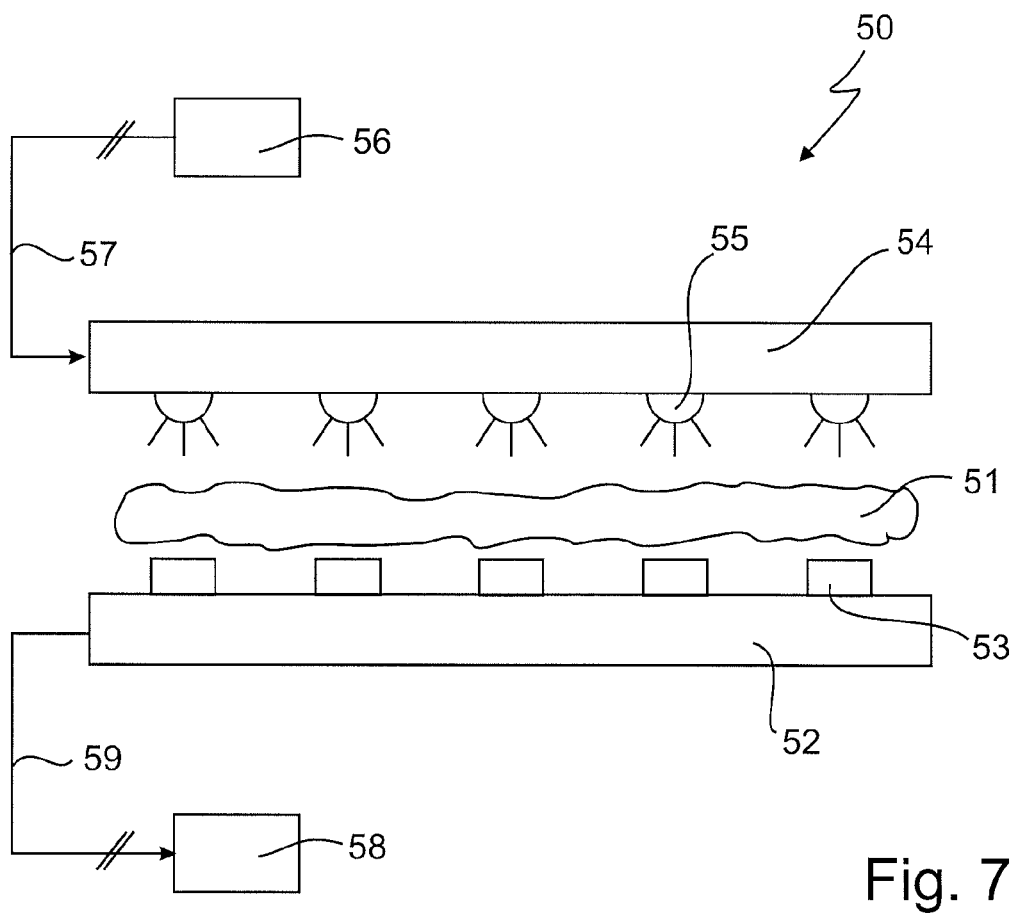
FIG. 7 shows a first embodiment of a testing device for cells, cell cultures and/or organotypic cell aggregates, which were equipped with light-sensitive channels.

FIG. 7 shows a testing device 50 for cells, cell cultures and/or organotypic cell aggregates 51, which were equipped with light-sensitive channels, for example by transfection with possibly viral vectors for the expression of e.g. channelrhodopsin-2.

The testing device 50 comprises an array 52 of microelectrodes 53 on which the cells, cell cultures and/or organotypic cell aggregates 51 are cultivated.

An array 54 of radiation-emitting elements 55 is arranged above the cells, cell cultures and/or organotypic cell aggregates 51; said array can lie on the cells, cell cultures and/or organotypic cell aggregates 51 and illuminate the latter in a spatially resolved fashion with electromagnetic radiation within and/or outside of the visible spectrum.

Furthermore, provision is made for an actuation device 56, which actuates, via a multi-core wire 57, the array 54 of radiation-emitting elements 55 for emitting spatially resolved electromagnetic radiation. This array 54 can be designed and operated like the above-described array 16, wherein the actuation device can be designed and operate like the above-described image receiver 13.

An evaluation unit 58 is connected to the array 52 via a multi-core wire 59 for detecting and evaluating signals which are emitted by the cells, cell cultures and/or organotypic cell aggregates 51 to the microelectrodes 53 upon illumination by the array 54.

Figure 8:
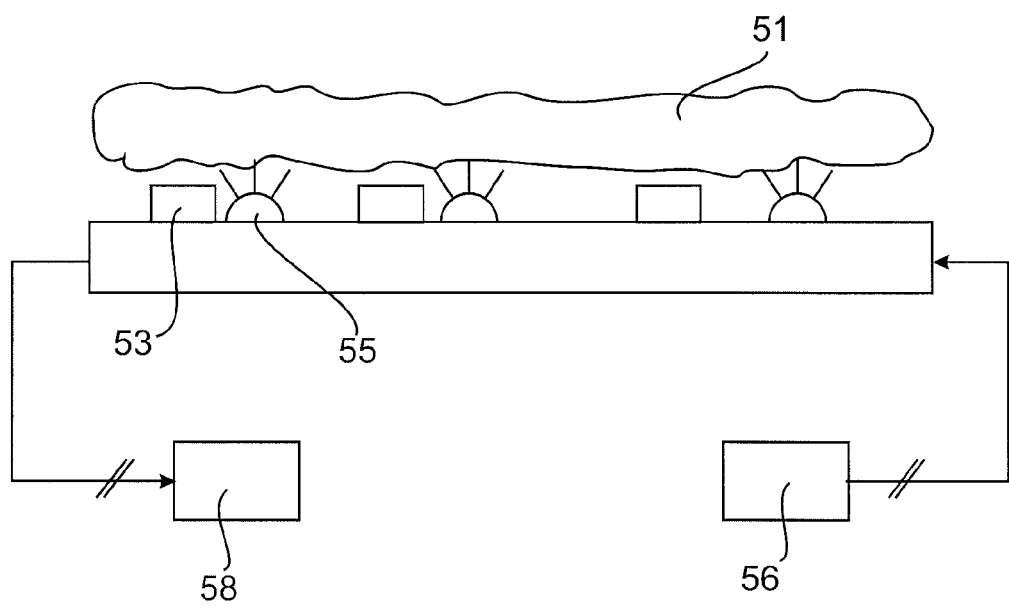
FIG. 8 shows a second embodiment of a testing device for cells, cell cultures and/or organotypic cell aggregates, which were equipped with light-sensitive channels.

As per FIG. 8, the radiation-emitting elements 55 can be integrated into the array 52 of microelectrodes 53 and so a local assignment can be set up between radiation-dependent excitation and emission of an electrical signal.

This affords the possibility of testing and optimizing, ex vivo, the function of the light-sensitive channels and/or the function of the array 54.

Figure 9:
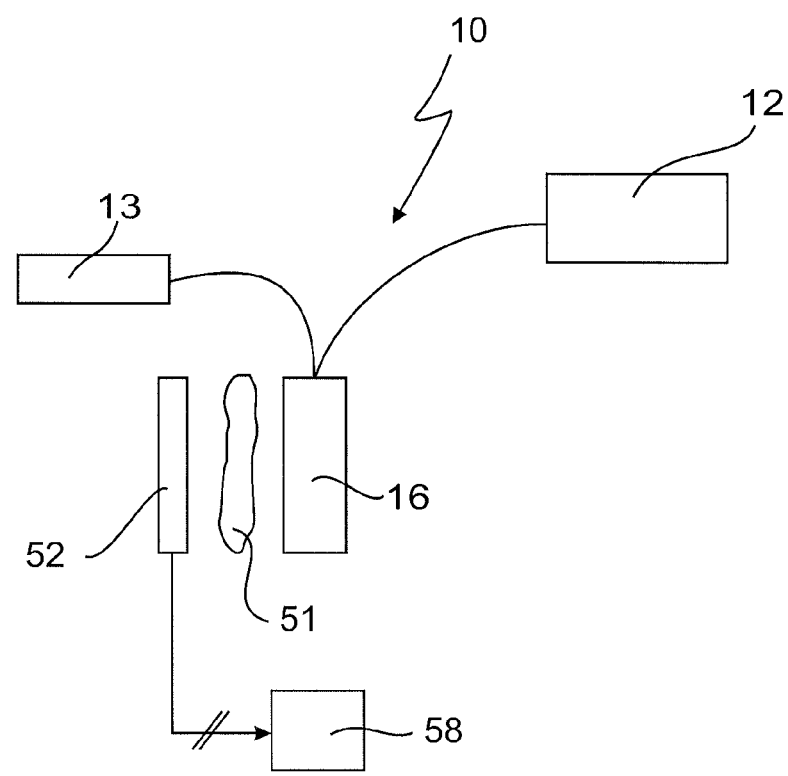
FIG. 9 shows an embodiment of a testing device for the novel retinal implant.

Accordingly, FIG. 9 shows a testing device for the novel retinal implant 10, as is shown in FIG. 6 above.

The cells, cell cultures and/or organotypic cell aggregates 51, which are illuminated by the retinal implant 10 in a spatially resolved fashion with electromagnetic radiation within and/or outside of the visible spectrum, are cultivated on the array 52 of microelectrodes disclosed in FIG. 7 and FIG. 8, wherein the array 16 is actuated via the image receiver 13.

The evaluation unit 58 is used to detect and evaluate signals, which are emitted by the cells, cell cultures and/or organotypic cell aggregates 51 during illumination of the image receiver 13 and corresponding emission of electromagnetic radiation to the microelectrodes by the array 16.

Thus, the retinal implant 10 can be tested and optimized, ex vivo, together with correspondingly modified cells.

Therefore, what is claimed is:

1. An active retinal implant to be implanted into an eye having a retina, comprising an array of stimulation elements that emit stimulation signals to cells of the retina, wherein the stimulation elements are radiation-emitting elements that emit optical stimulation signals for illuminating directly optically stimulating cells of the retina wherein the array of radiation-emitting elements are controlled by spatially resolved electrical signals converted from incident ambient light by an image receiver.

2. The retinal implant of claim 1, wherein the image receiver is an external image receiver, which is arranged outside of the eye.

3. The retinal implant of claim 1, wherein the image receiver is an implantable image receiver or image amplifier implantable into the eye.

4. The retinal implant of claim 3, wherein the implantable image receiver and the array of radiation-emitting elements are separate from one another.

5. The retinal implant of claim 4, wherein the implantable image receiver and the array of radiation-emitting elements are arranged on a flexible support.

6. The retinal implant of claim 5, wherein the implantable image receiver and the array of radiation-emitting elements are arranged next to one another on the support.

7. The retinal implant of claim 4, wherein the implantable image receiver and the array of radiation-emitting elements are arranged one above the other.

8. The retinal implant of claim 4, wherein the implantable image receiver and the array of radiation-emitting elements are integrated into a chip.

9. The retinal implant of claim 3, wherein the implantable image receiver and the array of radiation-emitting elements operate in different regions of the electromagnetic spectrum.

10. The retinal implant of claim 9, wherein the implantable image receiver processes electromagnetic radiation in the visible region of the spectrum, and the array of radiation-emitting elements radiates electromagnetic radiation outside of the visible region of the spectrum or in the near infrared region of the spectrum.

11. The retinal implant of claim 10, wherein the implantable image receiver comprises an optical filter, which optical filter blocks the spectrum of electromagnetic radiation emitted by the array of radiation-emitting elements.

12. The retinal implant of claim 3, wherein the implantable image receiver comprises an optical filter, which optical filter blocks the spectrum of electromagnetic radiation emitted by the array of radiation-emitting elements.

13. The retinal implant of claim 3, wherein the implantable image receiver and the array of radiation-emitting elements operate with a time offset.

14. The retinal implant of claim 1, wherein the radiation-emitting elements emit electromagnetic radiation within the visible spectrum.

15. The retinal implant of claim 1, wherein the radiation-emitting elements emit electromagnetic radiation outside of the visible spectrum.

16. The retinal implant of claim 1, wherein the radiation-emitting elements are light-emitting diodes or organic light-emitting diodes (OLEDs).

17. The retinal implant of claim 1, wherein the array of radiation-emitting elements comprises elements with different spectral radiation.

18. The retinal implant of claim 1, wherein the elements within the array of radiation-emitting elements are provided in a defined geometric arrangement.

19. The retinal implant of claim 1, wherein the elements within the array of radiation-emitting elements have a spacing between one another, wherein each element within the array of radiation-emitting elements reacts with a different population of cells of the retina.

20. An active retinal implant for implanting into an eye having a retina with a plurality of neurons comprising light sensitive channels comprising: an array of radiation-emitting elements that emit optical stimulation signals and an image receiver that converts incident ambient light into spatially resolved electrical signals, which electrical signals control the array of radiation-emitting elements, said radiation emitting elements radiating said optical stimulation signals onto said plurality of neurons.

21. The retinal implant of claim 20, wherein the image receiver and the array of radiation-emitting elements operate in different regions of the electromagnetic spectrum.

22. An active retinal implant for implanting into an eye having a retina with a plurality of neurons comprising light sensitive channels, comprising an array of radiation-emitting elements that emit optical stimulation signals said radiation emitting elements radiating said optical stimulation signals onto said plurality of neurons.

23. The retinal implant of claim 22, wherein the plurality of said neurons comprise and express channelrhodopsin-2, and wherein the radiation-emitting elements emit optical stimulation signals in the near infrared region of the spectrum.

* * * * *